United States Patent [19]

Link

[11] 3,976,428
[45] Aug. 24, 1976

[54] PROCESS FOR QUANTITATIVE ANALYSIS

[75] Inventor: John Link, St. Louis, Mo.

[73] Assignee: Petrolite Corporation, St. Louis, Mo.

[22] Filed: Apr. 5, 1972

[21] Appl. No.: 241,321

[52] U.S. Cl. .......................... 23/230 R; 23/230 M
[51] Int. Cl.² ........................................ G01N 21/24
[58] Field of Search ............... 23/230, 253; 252/408

[56] References Cited
UNITED STATES PATENTS

| | | | |
|---|---|---|---|
| 3,459,506 | 8/1969 | Finucane | 23/230 |
| 3,673,410 | 6/1972 | Waite et al. | 23/230 B |

Primary Examiner—R.E. Serwin
Attorney, Agent, or Firm—Sidney B. Ring; Hyman F. Glass

[57] ABSTRACT

A method for determining the concentration of the desired component of a system which comprises adding a predetermined amount of an easily analyzable auxiliary chemical to the system, which when subjected to analysis, for example spectroscopic analysis, gives a quantitative determination of its concentration in the system; and then determining the concentration of the desired component by correlating the ratio of the auxiliary chemical to the desired component.

5 Claims, 2 Drawing Figures

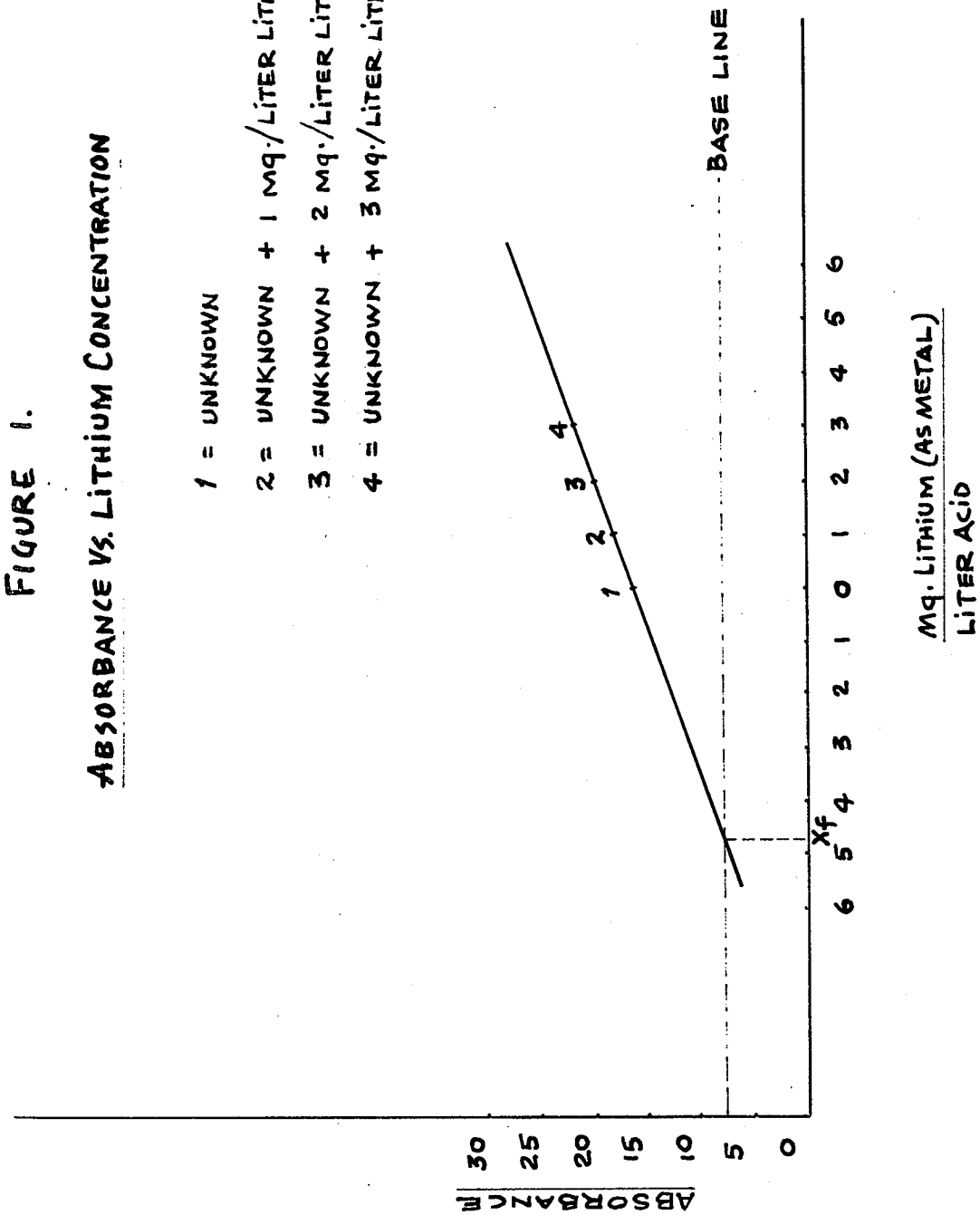

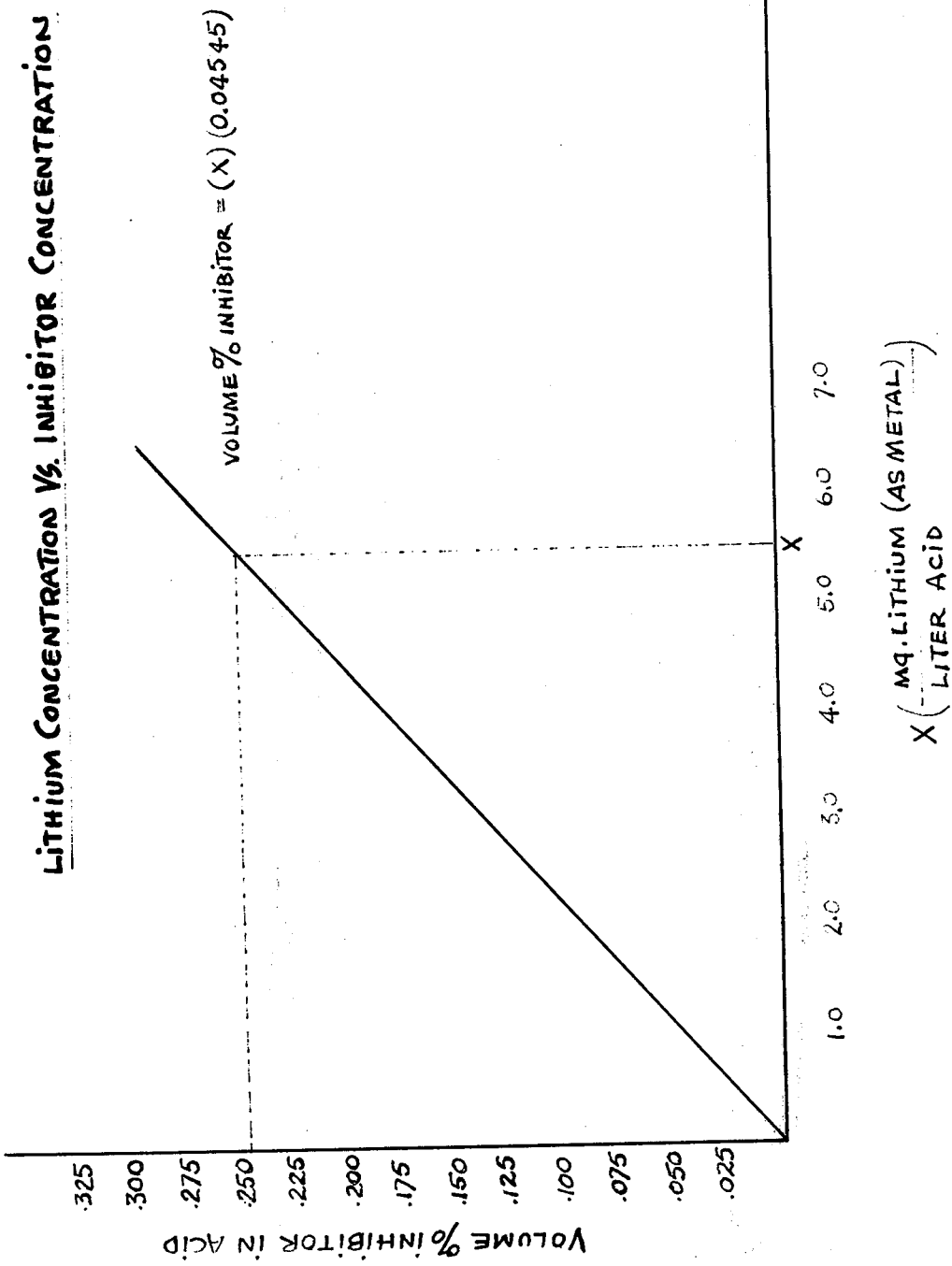

PROCESS FOR QUANTITATIVE ANALYSIS

In working with a chemical system it is highly desirable to be able to obtain a rapid determination of the concentration of a desired component of the system. This is not always easily done by direct analysis of the component itself.

I have now discovered a method of determining the concentration of a desired component in a system which comprises adding a predetermined amount of an easily analyzable auxiliary chemical to the system which when subjected to analysis gives a quantitative determination of its concentration in the system; and then determining the concentration of the desired component by correlating the ratio of the auxiliary chemical to the desired component.

In one embodiment, a salt, such as an alkali metal salt, for example LiCl, is added in predetermined amounts to a composition employed in treating a system, such as adding a predetermined amount of alkali metal salt such a LiCl to a corrosion inhibitor. When the LiCl-containing corrosion inhibitor is added to a corrosive system, an aliquot sample of the system is removed and its lithium concentration determined and correlated to the concentration of corrosion inhibitor.

Any suitable and convenient method may be employed. One convenient method is spectroscopic analysis such as exemplified by atomic absorption or emission spectroscopy. The preferred method of analysis is atomic absorption spectroscopy. A good discussion of this procedure can be found in "Atomic-Absorption Spectroscopy," by Ramirez-Munoz published by Elsevier Publishing Company, 1968.

The easily analyzable auxiliary chemicals of this invention can be employed with a wide variety of chemical treating agents including corrosion inhibitors, o/w and w/o demulsifiers, scale preventive, biocides such as bactericides, algicides, etc., water treating agents, agents employed in enhancing primary and secondary recovery, paraffin removers, etc.

Although a wide variety of chemical agents and systems can be employed, the invention will be illustrated with corrosion inhibitors. These are further illustrated by the preferred embodiment — corrosion inhibitors of the film-forming type.

In general, the film-forming organic corrosion inhibitors which are employed are generally heteropolar, for example, cationic or anionic in nature. The most widely used type of filmforming corrosion inhibitor is the cationic type, which is generally a comparatively high molecular weight organic compound containing one or more basic nitrogen atoms.

Anionic film-forming inhibitors contain hydrophobic groups, which have generally large hydrocarbon radicals, and acid groups.

In general, assuming a monomolecular layer, the more effective film-forming corrosion inhibitors are those which cover the largest area per molecule and form the most coherent and oriented film.

Typical but non-limiting examples, of film-forming corrosion inhibitors are presented below.

NITROGEN BASES

A wide variety of these compounds are known to be filmforming corrosion inhibitors. The following are a few nonlimiting examples:
1. Oxazolines (U.S. Pat. No. 2,587,955)
2. Tetrahydropyrimides (U.S. Pat. No. 2,640,029)
3. Imidazolines (U.S. Pat. No. Re. 23,227)
4. Pyrrolinedione (U.S. Pat. No. 2,466,530)
5. Amino amides (U.S. Pat. Nos. 2,550,682 and 2,598,213)
6. Quaternary amines (U.S. Pat. No. 2,659,693)
7. Monoamines, such as Rosin Amine (OIL GAS JOURNAL 46, No. 31, 91-6 (1956) ) Osyalkylated Rosin Amine (U.S. Pat. No. 2,564,749) Rosin Amine + solubilizing agent (U.S. Pat. Nos. 2,564,757 and 2,564,753)

CARBOXYLIC ACIDS

A wide variety of these compounds are known to be film-forming corrosion inhibitors. The following are non-limiting examples:
1. Naphthenic acids (U.S. Pat. Nos. 2,430,951 and 2,434,978)
2. Dimerized unsaturated fatty acids (U.S. Pat. Nos. 3,632,695)
3. Fatty acids, such as ricinoleic acid (U.S. Pat. Nos. 2,481,372 and 2,508,401)
4. Alkenyl succinic acids (British Pat. No. 567,089)

Acetylenic compounds such as propargyl alcohol and related compositions can also be employed alone or in conjunction with other corrosion inhibitors, as well as other compositions such as hexamethylene tetramine, etc.

USE IN CORROSION INHIBITORS FOR ACID SYSTEMS

The analyzable metal-containing compounds of this invention can be employed as corrosion inhibitors for acid systems, for example as illustrated by the following systems:
1. In the pickling of ferrous metals.
2. In the treatment of calcareous earth formations with acids such as HCl mixtures of HCl-HF, etc.
3. In spent sulfuric alkylation acid.
4. In byproduct HCl from the chlorination of organic compounds in the detergent, solvent, rubber, etc., industries.
5. In phosphoric and sulfuric acid systems employed in processing phosphate fertilizer.
6. In spent sulfuric acid from the process of reacting alkenes with alcohols, etc.

The above processes are illustrative. The corrosion inhibitors of this invention can be employed in any strong acid systems such as where $H_2SO_4$, HCl, $H_3PO_4$, HF, etc., are present.

USE AS PICKLING INHIBITORS

This phase of the invention relates to the use of an easily analyzable inhibitor in pickling. More particularly, the invention is directed to an easily analyzable pickling composition and to a method of pickling ferrous metal. The term "ferrous metal" as used herein refers to iron, iron alloys and steel.

To prepare ferrous metal sheet, strip, etc., for subsequent processing, it is frequently desirable to remove oxide coating, formed during manufacturing, from the surface. The presence of oxide coating, referred to as "scale" is objectionable when the material is to undergo subsequent processing. Thus, for example, oxide scale must be removed and a clean surface provided if satisfactory results are to be obtained from hot rolled sheet and strip in any operation involving deformation of the product. Similarly, steel prepared for drawing must possess a clean surface and removal of the oxide scale therefrom is essential since the scale tends to shorten drawing-die life as well as destroy the surface smoothness of the finished product. Oxide removal from sheet or strip is also necessary prior to coating operations to permit proper alloying or adherence of the coating to the ferrous metal strip of sheet. Prior to cold reduction, it is necessary that the oxide formed during hot rolling be completely removed to preclude surface irregularities and enable uniform reduction of the work.

The chemical process used to remove oxide from metal surfaces is referred to as "pickling." Typical pickling processes involve the use of aqueous acid solutions, usually inorganic acids, into which the metal article is immersed. The acid solution reacts with the oxides to form water and a salt of the acid. A common problem in this process is "overpickling" which is a condition resulting when the ferrous metal remains in the pickling solution after the oxide scale is removed from the surface and the pickling solution reacts with the ferrous base metal. An additional difficulty in pickling results from the liberated hydrogen being absorbed by the base metal and causing hydrogen embrittlement. To overcome the aforementioned problems in pickling, it has been customary to add corrosion inhibitors to the pickling solution.

The use of pickling inhibitors avoids or minimizes the abovedescribed problems in pickling ferrous metal articles and provides a pickling composition which minimizes corrosion, overpickling and hydrogen embrittlement. The pickling inhibitors not only prevent excessive dissolution of the ferrous base metal but effectively limit the amount of hydrogen absorption thereby during pickling.

When the easily analyzable compositions of this invention are employed in conjunction with pickling inhibitor they facilitate control and therefore the effectiveness of the inhibitor in the system.

Any metal capable of analysis by atomic absorption spectroscopy can be employed. The metals and salts thereof which are legion are described for example in above reference on "AtomicAbsorption Spectroscopy," by Ramirez-Munoz.

As a matter of practice, it is desirable to add a metal to the system in salt form which is not normally found in said system. Otherwise, unless correction is made to compensate for such presence of metals in the system, accurate results will not be obtained.

Therefore, any metal of the periodic system can be employed such as alkali metals, alkali earths, coinage metals, transition metals, zinc subgroup metals, etc. Since it is desirable to employ those metals not usually found in the system, the more exotic metals are generally employed such as lithium, rubidium, selenium, vanadium, cadmium, beryllium, cesium, nickel, cobalt, etc., in salt form such as in the form of halides, sulfates, acetates, carbonates, nitrates, phosphates, silicates, etc.

The following polyquaternaries are examples of inhibitors employed in acid systems which are useful in preparing the easily analyzable composition of this invention. These are described in Ser. No. 211,049, filed Dec. 22, 1971.

EXAMPLE 1

The reaction product of Still-bottom polyethylene polyamines (which contain primary, secondary and tertiary amino groups as well as heterocyclic amines) with ethylene dichloride having the general formula

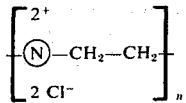

where $\textcircled{N}$ represents the polyamine.

EXAMPLE 2

The reaction product of Still-bottom polyethylene polyamines (which contain primary, secondary and tertiary amino groups as well as heterocyclic amines) with epichlorohydrin

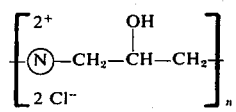

where $\textcircled{N}$ represents the polyamine.

EXAMPLE 3

The reaction product of diethylamine and 1,4-dichlorobutene

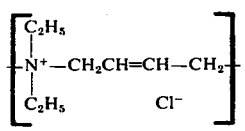

EXAMPLE 4

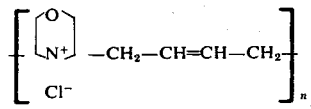

EXAMPLE 5

The reaction product of diethylamine and epichlorohydrin

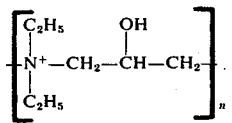

All of the above formulae are idealized formulae.

The above corrosion inhibitors are prepared in the following formulation:

| | |
|---|---|
| Corrosion inhibitor | 40% (by weight) |
| Propargyl alcohol | 5 |
| Methanol | 10 |
| Water | 45 |

The following example is presented for purposes of illustration and not of limitation, employing a HCl pickling corrosion inhibitor and LiCl as the easily analyzable composition. Although the invention is illustrated with a lithium salt, other salts of lithium or other metal salts can be employed. Graphs are employed to illustrate the invention.

FIG. 1 is a graph of absorbance plotted as a function of mg of lithium (calculated as Li) per liter of pickling acid.

FIG. 2 is a graph of volume percent of corrosion inhibitor in the pickling acid plotted as a function of lithium concentration (calculated as Li).

EXAMPLE A

An analyzable form of a corrosion inhibitor (Example 2) was prepared by adding sufficient LiCl so that it contained 2200 mg/liter of lithium, calculated as the element. A straight line relationship exists between lithium content and corrosion inhibitor concentration in fresh hydrochloric acid. The atomic absorption test procedure is designed to be run on fresh inhibited acid prior to pickling use to assure presence of the inhibitor in proper quantities.

A very accurate test method, utilizing the standard addition method of atomic absorption is used to determine the concentration of corrosion inhibitor in hydrochloric acid solutions. This test procedure should have an accuracy of well within + 5%, however, problems can be encountered if there is a great temperature difference between the inhibitor and the hydrochloric acid. If these conditions exist, what may actually be 0.25% by volume of inhibitor in acid at the time of addition may result in a different volume percent when the temperatures equilibrate. Since the inhibitor is added to the acid on a volume basis, this temperature effect will be present in any analytical procedure.

In the method of standard addition, net absorption readings are obtained on two types of solutions: "solution A", containing an aliquot of the unknown solution and "solution $S_n$", containing the same quantity of unknown solution plus measured amounts of a standard solution of the element. The measured absorption of all the samples is then plotted versus the concentrations of the element. The unknown concentration is usually plotted at zero while the samples containing the unknown plus the measured amounts of the element are plotted at the amount, in mg/liter, of element added to the unknown. The best straight line is then drawn for the data points and is extrapolated through the base line. The intercept of this curve at the base line is the amount of the element found in the unknown. Since a plot of absorbance versus concentration for lithium is linear over a small range, interference should be detectable by the following relationships.

$$K = (L_1 - H)_A/X \quad \text{(Formula 1)}$$

$$S_f = (L_n - L_1)/k \quad \text{(formula 2)}$$

where
$L_1$ = absorption reading of the unknown.
$L_n$ = absorption reading after addition of measured amount of element.
$H$ = base line or background reading.
$k$ = factor relating absorbance to concentration.
$X_f$ = concentration of unknown found from figure.
$S_n$ = amount of standard added.
$S_f$ = amount of addition standard found.

If $S_n$ does not equal $S_f$ then some sort of interference is present.

This interference can usually be corrected by the following formula:

(Formula 3)  $X$ actually present $= X_f \left(\dfrac{S_n}{S_f}\right)$

A sample of 20° Be. HCL containing 0.225% by volume of inhibitor was analyzed for lithium by the described method of standard additions. Sample 1 was the unknown and samples 2, 3 and 4 contained the unknown and an additional 1, 2 and 3 mg/l of lithium respectively. The base line was set at an absorbance reading of 8.0 and the four samples were run with the following results:

| Sample | Absorbance | mg/l Li added |
|---|---|---|
| 1 | 16.5 | 0 |
| 2 | 18.0 | 1 |
| 3 | 20.0 | 2 |
| 4 | 21.7 | 3 |

These results are plotted in FIG. 1. The intercept of the base line is at 4.8 mg/l. Using formulas (1) and (2) to check the consistency of the results, it is seen that the difference is slight.

$K = (L_1 - H)_A/X_f = (16.5 - 8.0)/4.8 = 1.77$
$S_f = (L_4 - L_1)/k = (21.7 - 16.5)/1.77 = 2.94$

Since $S_f$ does not equal $S$, which is 3, formula (3) is needed to correct $X_f$.

$$X = X_f \left(\dfrac{S_n}{S_f}\right) = 3.8 \left(\dfrac{3.0}{2.94}\right) = 4.9 \text{ mg/l L}.$$

Since the inhibitor contains 2200 mg/1 lithium, the theoretical amount of lithium in a 0.225% solution of inhibitor in HCL should be 4.95 mg/1. The 4.9 mg/1 of lithium would represent 0.223% by volume inhibitor in the HCL solution, according to FIG. 2.

The results of this example were obtained on a Perkin Elmer Model 303 Atomic Absorption Unit using air-acetylene fuel and a Perkin Elmer hollow cathode lithium lamp at a 1 mm slit and in the visible spectrum at a wavelength of 335 M.

As is quite evident, the easily analyzable auxiliary chemicals can be employed with other chemical treating agents and systems. It is, therefore, not only impossible to attempt a comprehensive catalogue of such agents and systems, but to attempt to describe the invention in its broader aspects in terms of specific chemical names of agents and systems used would be too voluminous and unnecessary since one skilled in the art could by following the disclosure select the proper agent. This invention lies in the use of easily analyzable auxiliary chemicals in chemical treating agents and systems and their individual composition is important only in the sense that their properties can effect this analyzable function.

To precisely define each chemical agent and system useful in this invention in light of the present disclosure would merely call for knowledge within the skill of the art in a manner analogous to a mechanical engineer who prescribes in the construction of a machine the proper materials and the proper dimensions thereof. From the description in this specification and with the knowledge of a chemist, one will know or deduce with confidence the chemical agents and systems suitable for this invention. In analogy to the case of a machine wherein the use of certain materials of construction or dimensions of parts would lead to no practical useful result, various materials will be rejected as inapplicable where others would be operative. One can obviously assume that no one will wish to make a useless composition or will be misled because it is possible to misapply the teachings of the present disclosure in order to do so.

Thus, any chemical agent or system where the easily analyzable auxiliary chemical can perform the intended function stated herein can be employed.

I claim:
1. A process for making a rapid quantitative determination of the amount of corrosion inhibitor in a metal pickling system which comprises
   1. adding a predetermined amount of easily analyzable lithium salt as an auxiliary chemical to said system,
   2. analyzing said system for the concentration of lithium salt by means of spectroscopic analysis and
   3. correlating the ratio of said lithium salt to said corrosion inhibitor so as to make a quantitative determination of its concentration in said system, thereby facilitating control and therefore the effectiveness of said corrosion inhibitor in said system.

2. The process of claim 1 where the metal to be treated in the metal pickling system is a ferrous metal.

3. The process of claim 1 where the corrosion inhibitor is a polyquaternary compound obtained by the reaction of a polyethylene polyamine with epichlorhydrin.

4. The process of claim 1 where the lithium salt is lithium chloride.

5. The process of claim 1 where the spectroscopic analysis is atomic absorption spectroscopy.

* * * * *